(12) United States Patent
Tsuyuki

(10) Patent No.: US 7,251,308 B2
(45) Date of Patent: Jul. 31, 2007

(54) X-RAY COMPUTED TOMOGRAPHY APPARATUS

(75) Inventor: Masaharu Tsuyuki, Nasu-gun (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 78 days.

(21) Appl. No.: 10/919,431

(22) Filed: Aug. 17, 2004

(65) Prior Publication Data
US 2005/0089133 A1 Apr. 28, 2005

(30) Foreign Application Priority Data
Aug. 25, 2003 (JP) ............................ 2003-300347

(51) Int. Cl.
*G01N 23/083* (2006.01)
(52) U.S. Cl. .............................. 378/8; 378/95; 600/428
(58) Field of Classification Search .................... 378/8, 378/95; 600/428
See application file for complete search history.

(56) References Cited

U.S. PATENT DOCUMENTS

| 2,190,389 | A | * | 2/1940 | Strauss et al. ................ 378/95 |
|---|---|---|---|---|
| 4,446,873 | A | * | 5/1984 | Groch et al. ................ 600/528 |
| 4,547,892 | A | * | 10/1985 | Richey et al. ................. 378/8 |
| 6,470,066 | B2 | * | 10/2002 | Takagi et al. .................. 378/8 |
| 6,504,894 | B2 | * | 1/2003 | Pan et al. ....................... 378/8 |
| 6,708,052 | B1 | * | 3/2004 | Mao et al. .................. 600/407 |
| 6,865,248 | B1 | * | 3/2005 | Rasche et al. ................. 378/8 |
| 7,020,511 | B2 | * | 3/2006 | Boyd et al. ................. 600/428 |
| 2003/0007593 | A1 | * | 1/2003 | Heuscher et al. .............. 378/4 |
| 2004/0077941 | A1 | * | 4/2004 | Reddy et al. ............... 600/428 |

FOREIGN PATENT DOCUMENTS

JP 2003-164446 6/2003

\* cited by examiner

*Primary Examiner*—Edward J. Glick
*Assistant Examiner*—Thomas R. Artman
(74) *Attorney, Agent, or Firm*—Oblon, Spivak, McClelland, Maier & Neustadt, P.C.

(57) ABSTRACT

An X-ray computerized tomographic apparatus comprising a gantry which scans a patient with X-rays in order to acquire data on the patient, a decision unit which decides completion of the acquisition of the data on the basis of an electrocardiac waveform of the patient, and a scan controller which controls the gantry in order to end the scan or irradiation with the X-rays when the completion of the data acquisition has been decided.

17 Claims, 7 Drawing Sheets

FIG. 3

| No. | SCAN MODE | START POSITION | END POSITION | CTD (mGy) | kV | mA | SCAN SPEED | NUMBER OF SLICES | HELICAL PITCH | RECONSTRUCTION MODE |
|---|---|---|---|---|---|---|---|---|---|---|
| 1 | HELICAL | 015.00 | 075.00 | 20 | 100 | 150 | 0.4 | 4 | 4.0 | ECG GATED, HALF SEGMENTS (3) |
|   |   |   |   |   |   |   |   |   |   |   |
|   |   |   |   |   |   |   |   |   |   |   |
|   |   |   |   |   |   |   |   |   |   |   |
|   |   |   |   |   |   |   |   |   |   |   |

Buttons: PATIENT INFORMATION, GANTRY INFORMATION, SCANOGRAM IMAGE, MAIN, RECONSTRUCTION CONDITION, WINDOW CONDITION, COPY, DELETE, BACK, DATA ACQUISITION COMPLETION CONDITION, VALIDATE

X-RAY COMPUTED TOMOGRAPHY APPARATUS

CROSS-REFERENCE TO RELATED APPLICATIONS

This application is based upon and claims the benefit of priority from prior Japanese Patent Application No. 2003-300347, filed Aug. 25, 2003, the entire contents of which are incorporated herein by reference.

BACKGROUND OF THE INVENTION

1. Field of the Invention

The present invention relates to an X-ray computerized tomographic apparatus which reconstructs an image under ECG gated reconstruction.

2. Description of the Related Art

An X-ray computerized tomographic apparatus provides information on a patient, in terms of an image on the basis of the intensity of X-rays transmitted through the patient. It plays important roles in a large number of medical services including the diagnoses, remedies and operation plans of diseases.

Cardiac examinations require high temporal resolutions. The requirement is chiefly coped with by adopting ECG gated reconstruction, or shortening a time period per revolution of an X-ray tube (heightening a rotational scan speed). In the ECG gated reconstruction, projection data corresponding to, for example, 3 heart beats are acquired. Data of close beat phases are extracted from the respective heart beats, so as to obtain a complete set of data for 360° or 180°+α (α:fan angle) as are necessary for image reconstruction. An image is reconstructed from the completed data.

JP-A-2003-164446 discloses a technique which obtains a complete set of data for 180°+α by excluding irregular heart beats, thereby to relieve artifacts. In this technique, a slice start position and a slice end position are determined beforehand, and a scan is ended at the point of time at which a scan position has reached the slice end position. Subsequently, the data for 180°+α are completed by excluding the data of the irregular heart beats from among data acquired from the slice start position to the slice end position which are previously set. Therefore, the number of heart beats from which the data for 180°+α have been collected can be settled only after the scan. Accordingly, a situation can occur where an intended temporal resolution has not been attained.

BRIEF SUMMARY OF THE INVENTION

An object of the present invention is to realize the generation of an image at an intended temporal resolution in an X-ray computerized tomographic apparatus which reconstructs the image by ECG gated reconstruction.

According to a first aspect of the present invention, there is provided an X-ray computerized tomographic apparatus comprising a scan unit which is configured for scanning a patient with X-rays in order to acquire data on the patient; a decision unit which is configured for deciding completion of the acquisition of the data on the basis of an electrocardiac waveform of the patient; and a control unit which is configured for controlling the scan unit in order to end the scan and/or irradiation with the X-rays when the completion of the data acquisition has been decided.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 3 is a diagram showing an example of a scan plan screen which is formed in an expert system in FIG. 1;

DETAILED DESCRIPTION OF THE INVENTION

Now, an embodiment of an X-ray computerized tomographic apparatus according to the present invention will be described with reference to the drawings. Incidentally, X-ray computerized tomographic apparatuses include various types such as a ROTATE/ROTATE type wherein an X-ray tube and a radiation detector rotate around a patient unitarily, and a STATIONARY/ROTATE type wherein a large number of detection elements are arrayed in the shape of a ring and wherein only an X-ray tube rotates around a patient. In this regard, the invention is applicable to any of the types. Here, the tomographic apparatus will be described as the rotate/rotate type which currently occupies the mainstream. Besides, in order to reconstruct tomogram data of one slice, projection data for about 360° are required in correspondence with one revolution around a patient, and projection data for 180°+α (α:fan angle) are required even with a half scan method. The invention is applicable to both the reconstruction schemes. Here, the half scan method will be described by way of example. In addition, regarding a mechanism for converting incident X-rays into charges, the mainstream is formed by an indirect conversion type in which the X-rays are converted into light by a fluorescent substance such as scintillator and in which the light is further converted into the charges by a photoelectric element such as photodiode, and a direct conversion type which utilizes the generation of electron-hole pairs within a semiconductor by the X-rays and the migrations of electrons and holes to electrodes, that is, a photoconductive phenomenon. Although either of the schemes may be adopted for an X-ray detection element, the former indirect conversion type will be referred to here. Meanwhile, in recent years, an X-ray computerized tomographic apparatus of so-called "multi-tube type" wherein a plurality of pairs of X-ray tubes and X-ray detectors are mounted on a rotating ring has been put into products, and the peripheral techniques thereof have been developed. The invention is applicable to both the conventional X-ray computerized tomographic apparatus of single-tube type and the X-ray computerized tomographic apparatus of the multi-tube type. Here, the single-tube type will be referred to.

Figure 1:
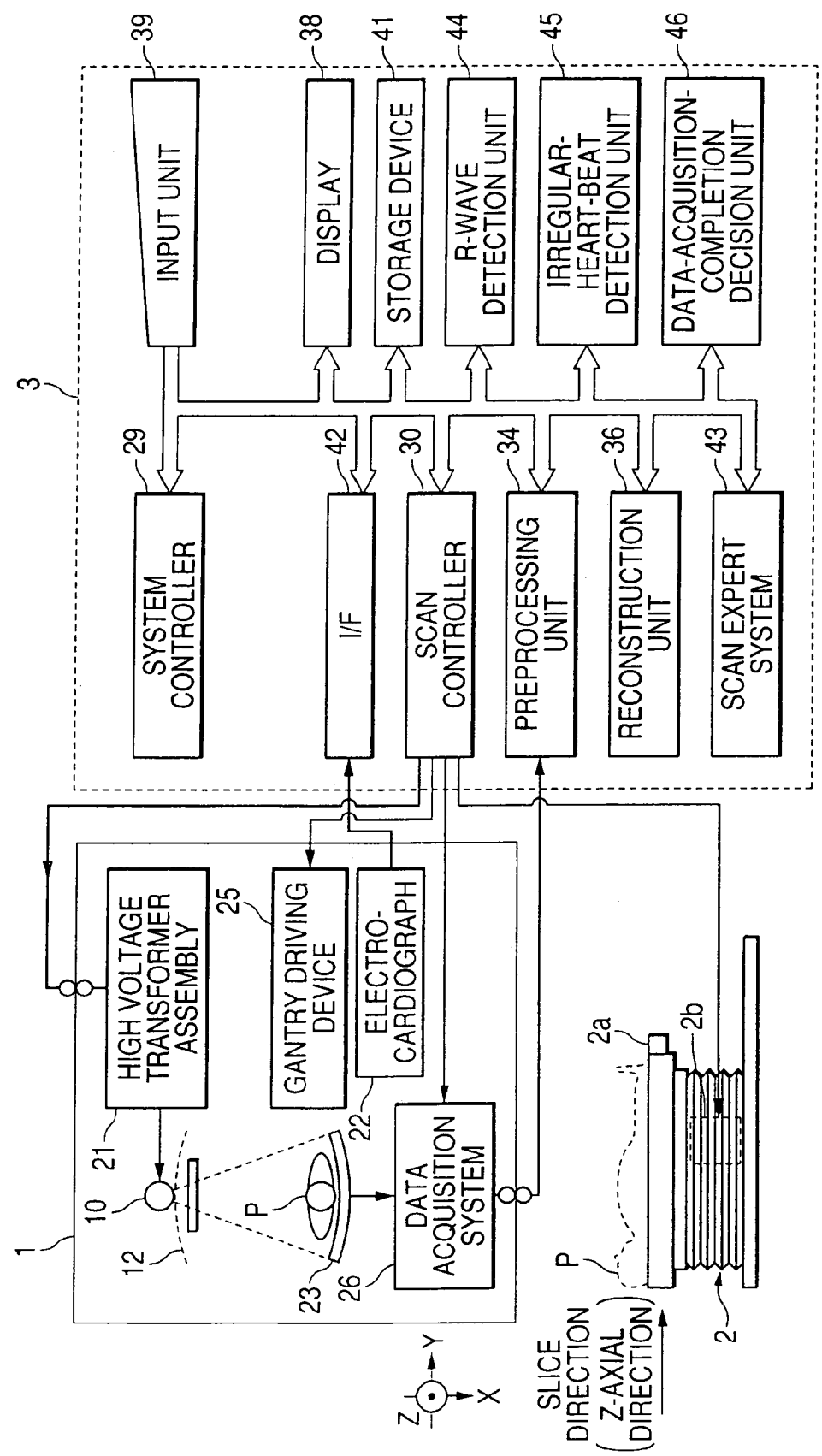
FIG. 1 is a block diagram showing the configuration of an X-ray computerized tomographic apparatus according to an embodiment of the present invention.

FIG. 1 shows the configuration of the X-ray computerized tomographic apparatus according to this embodiment. The X-ray computerized tomographic apparatus has a gantry 1 which is configured for acquiring projection data on a patient P. The gantry 1 includes an X-ray tube 10 and an X-ray detector 23. The X-ray tube 10 and the X-ray detector 23 are mounted on a ring-shaped rotating frame 12 which is rotationally driven by a gantry driving device 25. The central part of the rotating frame 12 is opened, and the patient P placed on the tabletop 2a of a diagnostic table 2 is inserted into the opening. In order to detect the electrocardiogram of the patient P, an electrocardiograph 22 is set on the patient P. The electrocardiograph 22 is connected to a computer unit 3 through an interface 42. Electrocardiac waveform data detected by the electrocardiograph 22 are accepted into the computer proper 3. The electrocardiograph 22 may be incorporated in the X-ray computerized tomographic apparatus as the constituent thereof, or it may well be an external equipment as the non-constituent of the X-ray computerized tomographic apparatus.

A tube voltage is applied across the cathode and anode of the X-ray tube 10 by a high voltage transformer assembly 21, and a filament current is fed from the high voltage transformer assembly 21 to the filament of the X-ray tube 10. X-rays are generated by the application of the tube voltage and the feed of the filament current. Either of a unidimensional array type detector and a two-dimensional array type detector may be adopted as the X-ray detector 23. Preferably the two-dimensional array type detector is adopted. Each X-ray detection element has a square photo-cathode of, for example, 0.5 mm×0.5 mm. Such X-ray detection elements in the number of, for example, 916 are arrayed as one row in a channel direction. Further, 40 rows, for example, are juxtaposed in a slice direction. Thus, the two-dimensional array type detector is constructed. The unidimensional array type detector is constructed of a single row.

Typically, the X-ray detector 23 is of two-dimensional array type which has the number of rows required for covering a heart region. In scanning the patient P, the tabletop 2a of the diagnostic table 2 is stopped. Thus, the X-ray tube 10 and the X-ray detector 23 are fixed at predetermined positions concerning the body axis direction of the patient P. Data are acquired in such a way that, with a slice position fixed, the X-ray tube 10 and the X-ray detector 23 are continuously rotated around the patient P.

A data acquisition system 26 generally abbreviated to "DAS", converts a signal outputted every channel from the detector 23, into a voltage signal, amplifies the voltage signal and converts the amplified signal into a digital signal. The data (raw data) are fed to the computer unit 3 outside the gantry 1. The preprocessing unit 34 of the computer unit 3 subjects the data (raw data) outputted from the data acquisition system 26, to correction processes such as a sensitivity correction, thereby to output the projection data. The projection data are sent to the storage device 41 of the computer system 3, and are stored therein together with the electrocardiac waveform data of the electrocardiograph 22.

The computer system 3 includes besides the preprocessing unit 34 and the storage device 41 mentioned above, a system controller 29, a scan controller 30, a reconstruction unit 36, a display 38, an input unit 39, a scan expert system 43, an R-wave detection unit 44, an irregular-heart-beat detection unit 45, and a data-acquisition-completion decision unit 46. The reconstruction unit 36 corresponds to the ECG gated reconstruction, and reconstructs image data out of a complete set of projection data for 360° or 180°+α as have been obtained from a plurality of heart beats. Especially, the reconstruction unit 36 here has the function of reconstructing the image data on the basis of data acquired in the periods of normal heart beats except irregular heart beats.

The R-wave detection unit 44 detects, for example, R-waves as feature waves from within an electrocardiac waveform. The irregular-heart-beat detection unit 45 detects the irregular heart beats from the intervals of the detected R-waves in accordance with a predetermined irregular-heart-beat detection condition.

The data-acquisition-completion decision unit 46 decides the completion of the data acquisition in accordance with a predetermined data acquisition completion condition. The number of heart beats is contained in the data acquisition completion condition. Besides, the data-acquisition-completion decision unit 46 decides the stop of the data acquisition in accordance with a predetermined data acquisition stop condition.

Two sorts of counting methods for the number of heart beats are prepared in this embodiment, and they are selectively used in compliance with the instructions of an operator. In the first counting method, since the start of the data acquisition, the irregular heart beats are excluded from counting, and only the normal heart beats are counted cumulatively. Accordingly, the counted number of heart beats becomes the total number of the normal heart beats since the start of the data acquisition, irrespective of whether the normal heart beats are continuous or discontinuous with the irregular heart beats intervening therebetween. On the other hand, in the second counting method, the irregular heart beats are excluded from counting, and only the normal heart beats are counted, since the start of the data acquisition as in the first counting method. In the second counting method, however, when the irregular heart beat has occurred, the number of counts is reset to zero, whereby the continuous number of the normal heart beats with no irregular heart beat intervening therebetween is counted.

Figure 2:
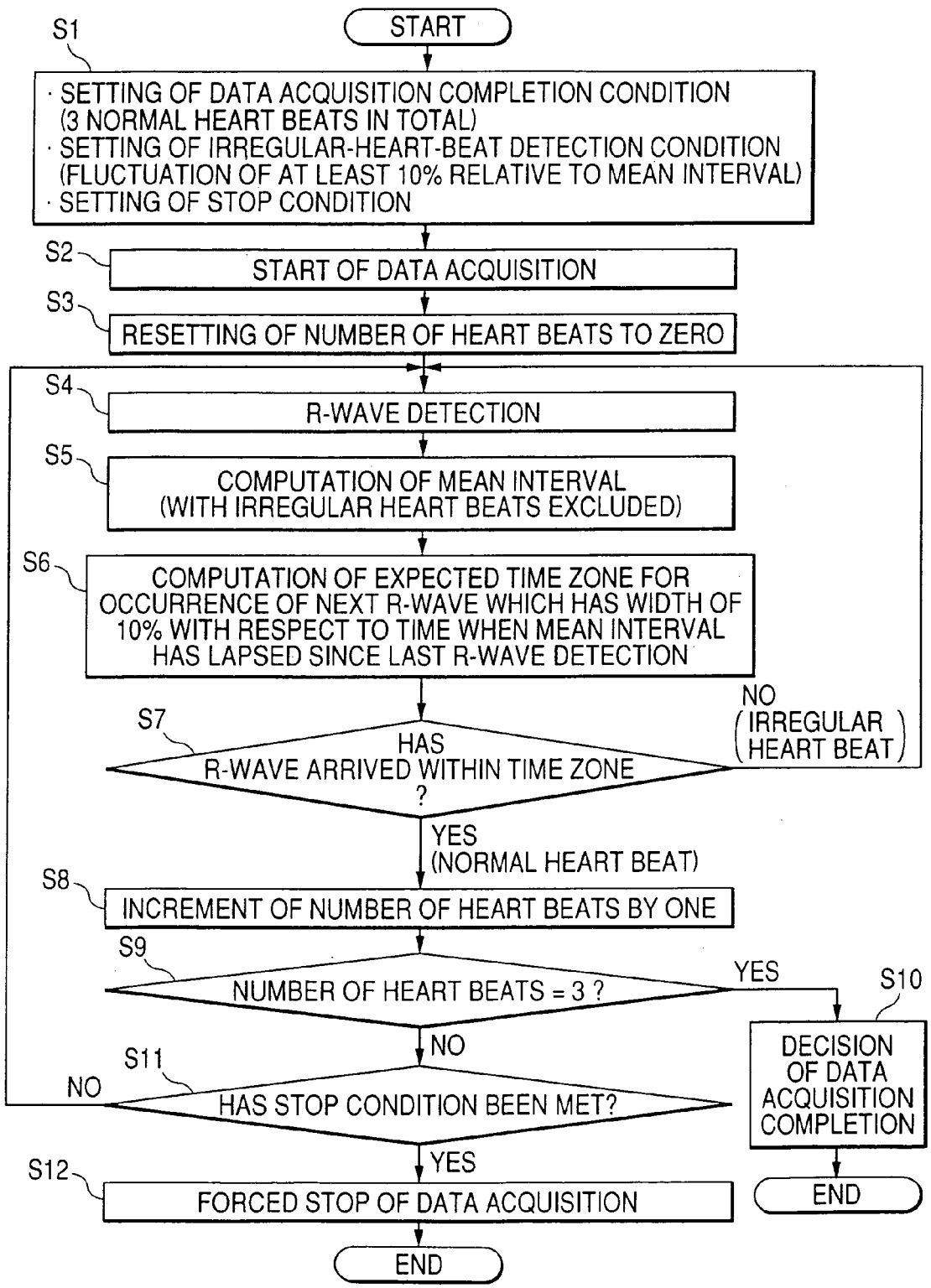
FIG. 2 is a flow chart showing operations which correspond to a first counting method in the embodiment.

FIG. 2 shows the operations of this embodiment corresponding to the first counting method. First of all, prior to data acquisition, a data acquisition completion condition, an irregular-heart-beat detection condition and a data acquisition stop condition are set at a step S1. The conditions are set at the stage of a scan plan. The scan plan is laid by the aid of the scan expert system 43. FIG. 3 shows an example of a scan plan screen which is formed by the scan expert system 43. Displayed on the scan plan screen together with patient information, gantry information and a scanogram image, are a part to-be-photographed which has been designated or selected by an operator, and a scan condition, a reconstruction condition and a window condition which have been planned by the scan expert system 43 in accordance with an examination plan. By way of example, the scan condition contains a scan mode, a scan start position, a scan end position, "CTDI" (CT Dose Index) which represents an exposed dose stipulated by the Food and Drug Administration of U.S., a tube voltage "kV", a tube current "mA", a scan speed, the number of slices (the number of rows for use), a helical pitch, and a reconstruction mode. At the lower part of the scan plan screen, a button expressed as "Data acquisition completion condition" is arranged together with buttons expressed as "Copy", "Delete", "Back" and "Validate".

Figure 4:
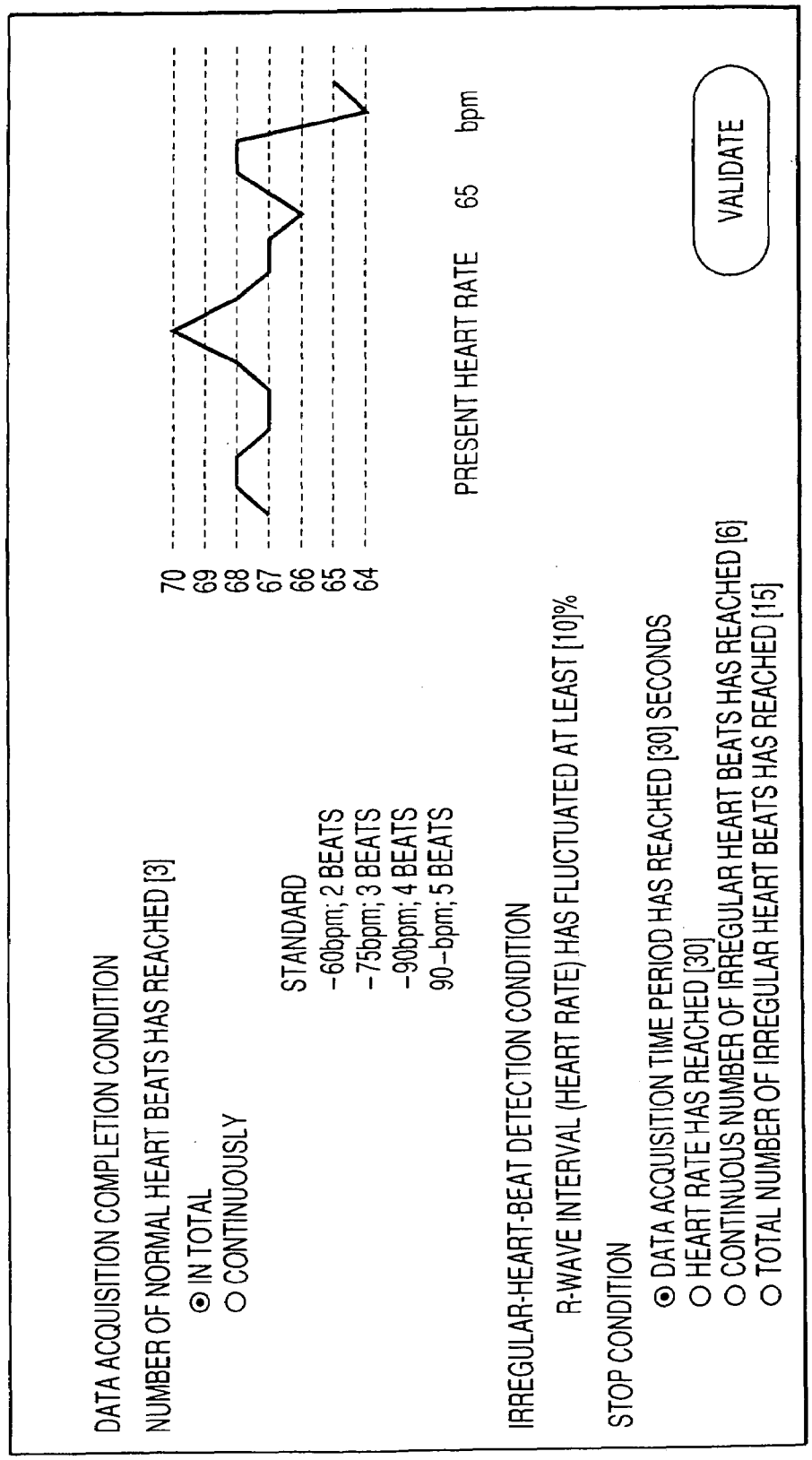
FIG. 4 is a diagram showing an example of a "data acquisition completion condition" setting window which is popped up by clicking a button "Data acquisition completion condition" in FIG. 3.

When the operator has clicked the button expressed as "Data acquisition completion condition", the scan expert system 43 forms a data acquisition completion condition window shown in FIG. 4. The data acquisition completion condition window is displayed on the scan plan screen of FIG. 3 in popped-up fashion. The window contains a region for setting the data acquisition completion condition, a region for setting the irregular-heart-beat detection condition, a region for displaying the electrocardiac waveform and the number of heart beats of the patient P, and a region for setting the data acquisition stop condition.

The scan expert system 43 has the two sorts of conditions made ready for the data acquisition completion condition. Both the conditions are identical in that the data acquisition is completed when the number of normal heart beats except irregular heart beats has reached a predetermined number since the start of a scan, but they differ in the counting method for the number of heart beats. In one counting method, the total number of the normal heart beats is counted, whereas in the other counting method, the continuous number of the normal heart beats is counted. In the setting region for the data acquisition completion condition, the choices of the counting methods are displayed together with a column for inputting a preset number. In the ECG gated reconstruction, the number of heart beats for acquiring data which are required for realizing a predetermined temporal resolution is substantially determined in accordance with a heart rate. By the way, the temporal resolution of computerized tomography can be usually defined as a scan speed, in other words, a time period for projection data used in the reconstruction of one image, but in the ECG gated reconstruction, the temporal resolution is fundamentally obtained as a value which is found by dividing the acquiring time period by the number of heart beats for the data acquisition. The scan expert system 43 evaluates the heart rate from the inverse number of the interval of R-waves (heart beat period) detected by the R-wave detection unit 44, and it initially displays the number of heart beats corresponding to the evaluated heart rate, as a recommended value. If necessary, the operator alters the recommended value to a desired value through the input unit 39. When the operator desires a higher temporal resolution (a shorter temporal width), he/she revises the number of heart beats to a value higher than the recommended value. In contrast, when a low temporal resolution suffices, the operator revises the number of heart beats to a value lower than the recommended value, in consideration of the relief of a burden on the patient P, or the like.

An irregular-heart-beat detection method to be explained here is an example which utilizes the fluctuation rate of the R-wave interval (or heart rate) relative to the mean interval (or mean heart rate) of, e.g., immediately preceding 10 heart beats, but any desired method may be adopted without being restricted to the example. The limitation of the fluctuation rate can be set by specifying as an irregular heart beat to-be-detected, the least percentage value of the fluctuation of the R-wave interval relative to the mean interval. As an initial candidate value, when the R-wave interval has fluctuated at least 10% relative to the mean interval, the corresponding heart beat is detected as the irregular heart beat, but it is a matter of course that the candidate value can be revised to any desired value. In the ensuing description, it will be assumed for the sake of convenience that the preset number of heart beats be 3, and that the limitation of the fluctuation rate be 10%.

Broadly, four choices are prepared as the data acquisition stop condition. With the first choice, when an elapsed time since the time point of the start of the data acquisition has reached any set time period such as 30 seconds, the data acquisition is stopped even if not completed. With the second choice, when the number of heart beats has reached any set number such as 30 since the start time point of the data acquisition irrespective of normal and irregular heart beats, the data acquisition is stopped even if not completed. With the third choice, when the continuous number of irregular heart beats has reached any set number such as 6, the data acquisition is stopped even if not completed. Herein, as an alternative aspect, when the duration of an irregular heart beat has reached any set time period, the data acquisition is stopped even if not completed. With the fourth choice, when the total number of irregular heart beats (or the total time period of irregular heart beats) has reached any set number (or any set time period) such as 15 since the start of the data acquisition irrespective of whether the irregular heart beats are continuous or discontinuous, the data acquisition is stopped even if not completed.

Figure 5:
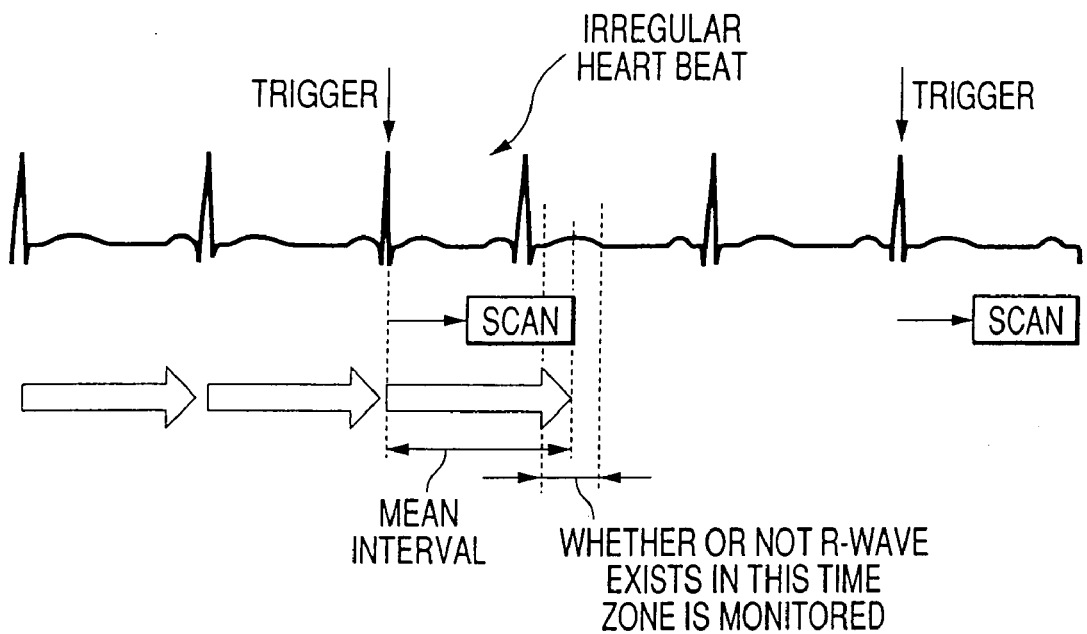
FIG. 5 is a supplementary diagram for a step S7 in FIG. 2.

Referring back to FIG. 2, after the scan plan settings have been made, the data acquisition is started (S2). At the start of the data acquisition, the data-acquisition-completion decision unit 46 resets the number of heart beats (count value) to zero (S3). The R-wave detection unit 44 detects an R-wave from electrocardiac waveform data sent from the electrocardiograph 22 (S4). The irregular-heart-beat detection unit 45 computes the mean interval of R-waves which correspond to immediately preceding 10 heart beats (S5). Subsequently, the irregular-heart-beat detection unit 45 computes an expected time zone for the occurrence of an R-wave, subject to a normal heart beat which has a time width of 10% of the mean interval with the center point at a time when the R-wave mean interval has lapsed since the last time of the R-wave (S6). Further, as shown in FIG. 5, the irregular-heart-beat detection unit 45 waits for the detection of the next R-wave, and it judges the corresponding heart beat as a normal one when the detected R-wave has occurred within the computed time zone, whereas it judges the corresponding heart beat as an irregular one when the detected R-wave has arrived outside the computed time zone, in other words, has occurred before or after this time zone (S7).

When the R-wave has not arrived within the expected time zone, the data-acquisition-completion decision unit 46 maintains the number of heart beats (count value), in other words, it excludes the irregular heart beat from counting, and the routine returns to the step S4, at which the detection of the next R-wave is waited for.

When the R-wave has arrived within the expected time zone, the data-acquisition-completion decision unit 46 increments the number of heart beats (count value) by one (S8). Thus, only normal heart beats are used for the counting. Whether or not the incremented number of heart beats has reached a preset number (here, 3), is decided (S9). When the number of heart beats has not reached the preset number, the routine proceeds via a data acquisition stop decision (S11) back to the step S4, at which the detection of the next R-wave is waited for. When a data acquisition stop has been decided at the step S11, the data acquisition is stopped (S12) even if not completed.

Figure 6:
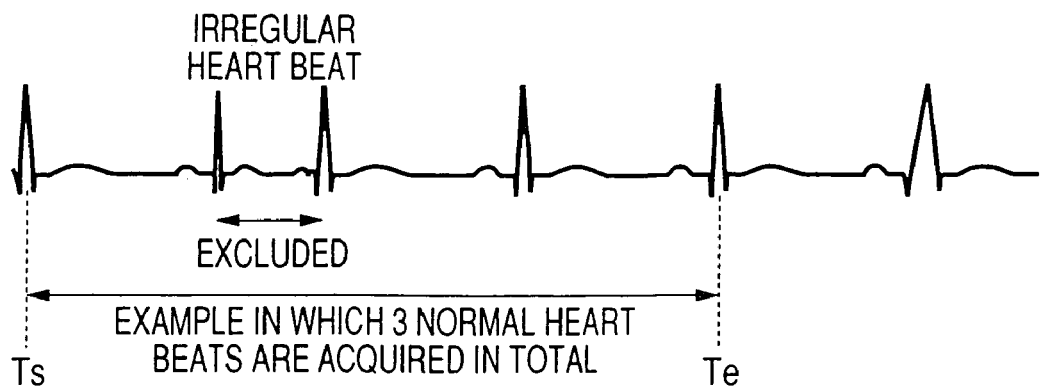
FIG. 6 is a diagram showing a data acquisition completion time point Te which is decided at a step S10 in FIG. 2.

When the number of heart beats has reached the preset number, the data-acquisition-completion decision unit 46 decides the completion of the data acquisition (S10), and it feeds the scan controller 30 with a signal representative of the data acquisition completion at a time Te in FIG. 6. The scan controller 30 which has received the signal representative of the data acquisition completion, controls the high voltage transformer assembly 21 to stop the generation of X-rays, controls the gantry driving device 25 to stop the rotation of the X-ray tube 10 as well as the X-ray detector 23, and controls the data acquisition system 26 to stop the data acquisition. According to the data acquisition completion condition, the data of views corresponding to irregular heart beats can be acquired in the periods of normal heart beats.

As thus far described, according to the first counting method, data which correspond to normal heart beats with irregular heart beats excluded can be reliably acquired in the required number of heart beats, and a temporal resolution intended in the ECG gated reconstruction can be achieved.

Figure 7:
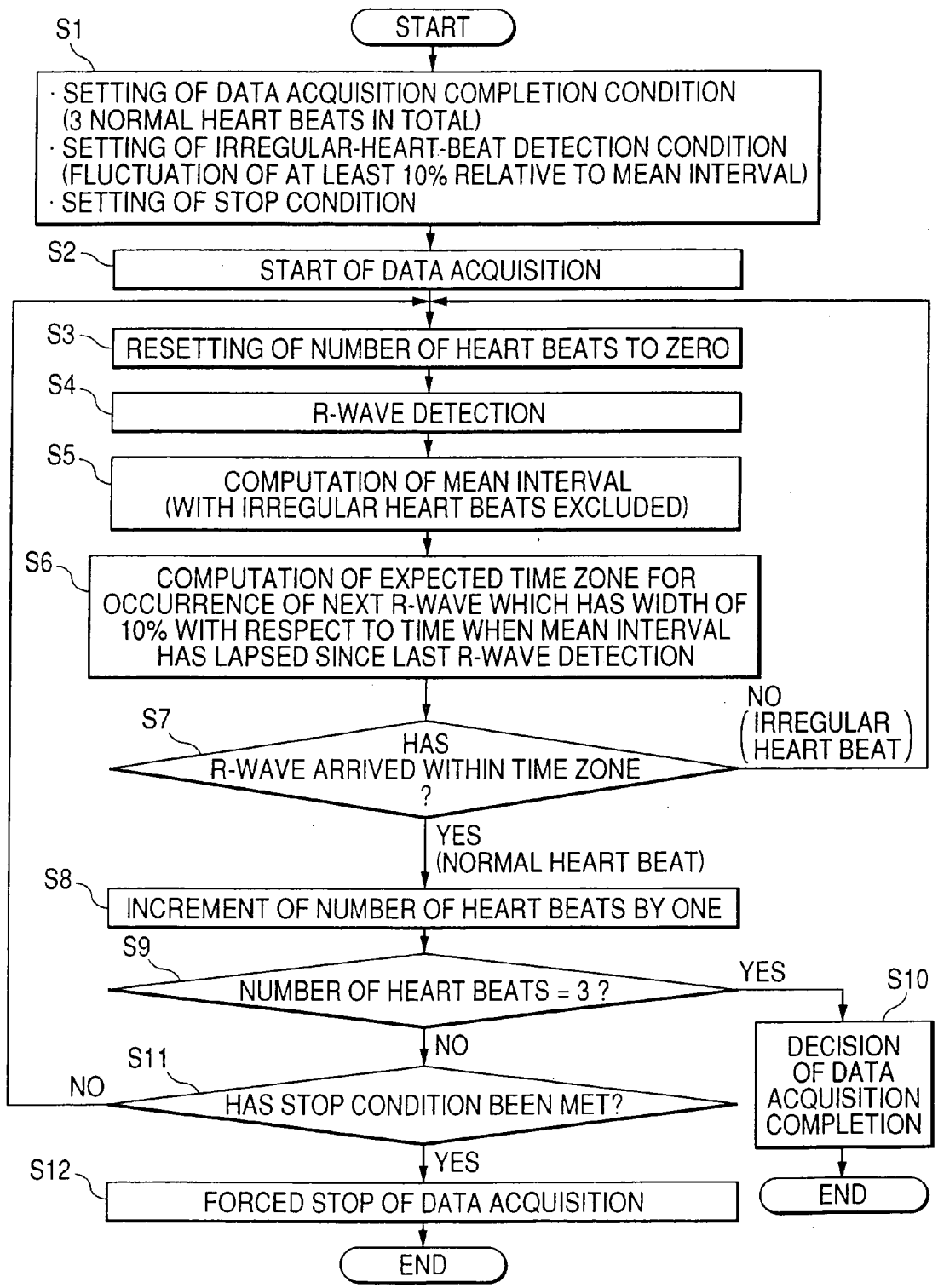
FIG. 7 is a flow chart showing operations which correspond to a second counting method in the embodiment.
Figure 8:
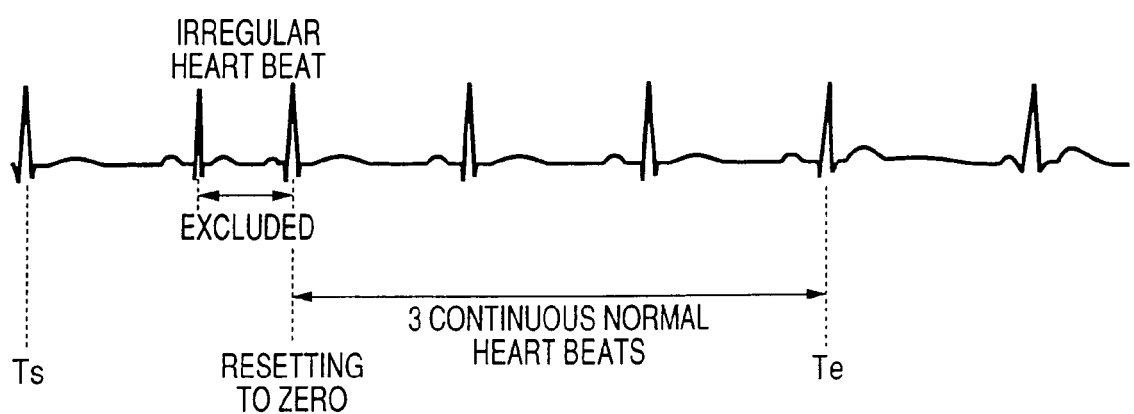
FIG. 8 is a diagram showing a data acquisition completion time point Te which is decided at a step S10 in FIG. 7.

FIG. 7 shows the steps of the second counting method. The point of difference of the second counting method from the first one is as stated below. In the first counting method, when an irregular heart beat has occurred, the number of heart beats (count value) obtained till then is maintained, and the next normal heart beat is continuously counted from the maintained count value. Thus, the completion of data acquisition is decided, not only when the preset number of normal heart beats have occurred continuously, but also when the preset number of normal heart beats have occurred discontinuously with one or more irregular heart beats intervening therebetween. On the other hand, in the second counting method, when an irregular heart beat has occurred (S7), the routine returns to the step S3, at which the number of heart beats (count value) obtained till then is reset to zero, and the counting of normal heart beats is started anew. Thus, as shown in FIG. 8, the completion of data acquisition is decided only when the preset number of normal heart beats have occurred continuously.

In the above description, the data-acquisition-completion decision unit 46 operates upon the occurrence of an irregular heart beat, to exclude the irregular heart beat from counting and to restart the counting from the next normal heart beat. However, when an irregular heart beat has occurred, the decision unit 46 may well operate to exclude, not only the irregular heart beat, but also even a normal heart beat subsequent to this irregular heart beat, from counting, and to restart the counting from the still next heart beat. In the case of ceasing the counting for the time period between the irregular heart beat and the next heart beat in this manner, it is possible to preventively avoid, for example, a situation where, although a heart beat period is normal, the electrocardiac waveform (cardiac motion) of the next heart beat is in disorder due to the irregular heart beat.

By the way, in case of half reconstruction (using only one segment) by performing "S & S" (scan & scan: continuous conventional scans of a plurality of slice positions), when an irregular heart beat has been detected, an identical slice position is scanned again without shifting to the next slice position.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computerized tomographic apparatus, comprising:
    a scan unit configured to scan a patient with X-rays in order to acquire data on the patient;
    a decision unit configured to decide completion of the acquisition of the data based on an electrocardiac waveform of the patient such that a period of the scanning includes at least one heart beat; and
    a control unit configured to control said scan unit in order to end the scan and/or irradiation with the X-rays when the completion of the data acquisition has been decided,
    wherein said decision unit includes an irregular-heart-beat detection unit configured to detect an irregular heart beat based on the electrocardiac waveform of the patient; and
    wherein said decision unit is configured to render the decision in order to acquire data of a view corresponding to the irregular heart beat.

2. The X-ray computerized tomographic apparatus according to claim 1, further comprising:
    a reconstruction unit configured to reconstruct image data based on data acquired in normal heart beat periods, excluding the irregular heart beat.

3. The X-ray computerized tomographic apparatus according to claim 1, wherein said control unit is configured to extend a time period for the data acquisition when the irregular heart beat has been detected.

4. The X-ray computerized tomographic apparatus according to claim 1, wherein said decision unit is configured to count the number of heart beats except the irregular heart beat since a start of the data acquisition, and to decide the completion of the data acquisition when the counted number has reached a preset number.

5. The X-ray computerized tomographic apparatus according to claim 1, wherein said decision unit is configured to count a total number of heart beats except the irregular heart beat since a start of the data acquisition.

6. The X-ray computerized tomographic apparatus according to claim 1, wherein said decision unit is configured to count the continuous number of heart beats except the irregular heart beat since a start of the data acquisition.

7. The X-ray computerized tomographic apparatus according to claim 1, wherein said decision unit is configured to count the number of heart beats except a heart beat subsequent to the irregular heart beat, when the irregular heart beat has been detected.

8. The X-ray computerized tomographic apparatus according to claim 1, further comprising:
    an input-screen creation unit configured to create a screen in order to input a condition concerning the completion of the data acquisition.

9. An X-ray computerized tomographic apparatus according to claim 8, wherein the input screen contains choices for selecting which of a total number and a continuous number is to be counted as the number of heart beats.

10. An X-ray computerized tomographic apparatus according to claim 8, wherein the input screen contains candidates for a preset counted number corresponding to the number of heart beats of the patient.

11. The X-ray computerized tomographic apparatus according to claim 1, wherein said decision unit is configured to decide ending of the data acquisition together with the completion thereof.

12. The X-ray computerized tomographic apparatus according to claim 11, wherein said decision unit is configured to decide the ending of the data acquisition upon lapse of a predetermined time period since a start of the data acquisition.

13. The X-ray computerized tomographic apparatus according to claim 11, wherein said decision unit is configured to decide the ending of the data acquisition when the number of heart beats since a start of the data acquisition has reached a predetermined number.

14. The X-ray computerized tomographic apparatus according to claim 11, wherein said decision unit is configured to decide the ending of the data acquisition when the continuous number or the total number of such irregular heart beats since a start of the data acquisition has reached a predetermined number.

15. The X-ray computerized tomographic apparatus according to claim 11, wherein said decision unit is configured to decide the ending of the data acquisition when a duration of the irregular heart beat or a total time period of such irregular heart beats since a start of the data acquisition has reached a predetermined time period.

16. An X-ray computerized tomographic apparatus according to claim 11, wherein said scan unit includes an X-ray tube and an X-ray detector of two-dimensional array type, the X-ray tube and the X-ray detector are fixed at predetermined positions concerning a body axis direction of the patient, and the X-ray tube and the X-ray detector are continuously rotated around the patient, thereby to acquire the data.

17. An X-ray computerized tomographic apparatus, comprising:
- a scan unit configured to scan a patient with X-rays in order to acquire data on the patient;
- a decision unit configured to decide completion and ending of the data acquisition based on a number of irregular heart beats or normal heart beats of the patient such that a period of the scanning includes at least one heart beat; and
- a control unit configured to control said scan unit in order to end the scan and/or irradiation with the X-rays when either of the completion and ending of the data acquisition has been decided,
- wherein said decision unit includes an irregular-heart-beat detection unit configured to detect an irregular heart beat based on the electrocardiac waveform of the patient; and
- wherein said decision unit is configured to render the decision in order to acquire data of a view corresponding to the irregular heart beat.

* * * * *